(12) United States Patent
Neister

(10) Patent No.: US 9,700,642 B2
(45) Date of Patent: Jul. 11, 2017

(54) METHOD AND APPARATUS FOR STERILIZING AND DISINFECTING AIR AND SURFACES AND PROTECTING A ZONE FROM EXTERNAL MICROBIAL CONTAMINATION

(71) Applicant: S. Edward Neister, Dover, NH (US)

(72) Inventor: S. Edward Neister, Dover, NH (US)

( * ) Notice: Subject to any disclaimer, the term of this patent is extended or adjusted under 35 U.S.C. 154(b) by 142 days.

(21) Appl. No.: 14/254,957

(22) Filed: Apr. 17, 2014

(65) Prior Publication Data
US 2014/0227132 A1    Aug. 14, 2014

Related U.S. Application Data

(63) Continuation-in-part of application No. 11/831,667, filed on Jul. 31, 2007, now Pat. No. 8,753,575, which
(Continued)

(51) Int. Cl.
*A61L 2/10* (2006.01)
*A61L 2/00* (2006.01)
(Continued)

(52) U.S. Cl.
CPC ............... *A61L 2/10* (2013.01); *A23B 7/015* (2013.01); *A23L 3/28* (2013.01); *A61L 2/0011* (2013.01); *A61L 9/20* (2013.01); *B08B 17/00* (2013.01)

(58) Field of Classification Search
CPC . A61L 2/10; A61L 2/0011; A61L 9/20; A23L 3/28; A23B 7/015; B08B 17/00
See application file for complete search history.

(56) References Cited

U.S. PATENT DOCUMENTS 3,672,126 A    6/1972  Goettle
4,317,041 A    2/1982  Schenck
(Continued)

FOREIGN PATENT DOCUMENTS

CN    2139811 Y    8/1993
CN    2604181 Y    2/2004
(Continued)

OTHER PUBLICATIONS

U.S. Appl. No. 60/543,710, Feb. 11, 2004.*

*Primary Examiner* — Regina M Yoo
(74) *Attorney, Agent, or Firm* — Lambert & Associates; Gary E. Lambert; David J. Connaughton, Jr.

(57) ABSTRACT

This invention relates to a method, process and apparatus for disinfecting and sterilizing all types of surfaces contaminated with microorganisms and toxic substances to render both inactive. Furthermore, this invention relates to both a method and apparatus for disinfecting and/or sterilizing breathable air and then using this air to protect a confined space from external contamination. The apparatus consists of a new ultra-violet (NUV) source that is more effective than mercury based 254 nm light for destroying DNA of virus, bacteria, spores and cysts. It is most effective in breaking chemical bonds in toxic gases and Biotoxins that are useful to terrorists. It is combined with other apparatus that remove particulates and byproducts sometimes produced by the NUV source and maintains positive pressure of the confined space so as to prevent the influx of air from outside the protected zone.

18 Claims, 10 Drawing Sheets

Related U.S. Application Data is a continuation-in-part of application No. PCT/US2006/003393, filed on Jan. 31, 2006.

(60) Provisional application No. 60/593,626, filed on Jan. 31, 2005.

(51) Int. Cl.
*A61L 9/20* (2006.01)
*B08B 17/00* (2006.01)
*A23B 7/015* (2006.01)
*A23L 3/28* (2006.01)

(56) References Cited

U.S. PATENT DOCUMENTS

| | | | |
|---|---|---|---|
| 4,458,153 A | 7/1984 | Wesley | |
| 4,524,079 A | 6/1985 | Hofmann | |
| 5,364,645 A | 11/1994 | Lagunas-Solar et al. | |
| 5,492,676 A | 2/1996 | Katatani et al. | |
| 5,505,904 A | 4/1996 | Haidinger et al. | |
| 5,647,890 A * | 7/1997 | Yamamoto | B03C 3/155 95/69 |
| 5,750,072 A | 5/1998 | Sangster et al. | |
| 5,753,106 A | 5/1998 | Schenck | |
| 5,843,374 A * | 12/1998 | Sizer | A23L 3/28 422/24 |
| 5,933,702 A * | 8/1999 | Goswami | A61L 9/205 422/186.3 |
| 5,993,738 A | 11/1999 | Goswani | |
| 6,063,170 A * | 5/2000 | Deibert | A61L 9/015 261/80 |
| 6,099,799 A | 8/2000 | Anderson | |
| 6,149,717 A | 11/2000 | Satyapal et al. | |
| 6,160,835 A * | 12/2000 | Kwon | B23K 26/06 219/121.68 |
| 6,165,170 A * | 12/2000 | Wynne | A61B 18/203 606/10 |
| 6,235,090 B1 | 5/2001 | Bernstein et al. | |
| 6,673,137 B1 * | 1/2004 | Wen | A61L 9/015 422/121 |
| 6,770,069 B1 * | 8/2004 | Hobart | A61B 18/203 128/898 |
| 7,326,387 B2 | 2/2008 | Arts et al. | |
| 2002/0089275 A1 * | 7/2002 | Falkenstein | A61L 2/10 313/29 |
| 2002/0177118 A1 * | 11/2002 | Coogan, Jr. | A61M 1/3681 435/2 |
| 2003/0170151 A1 * | 9/2003 | Hunter | A61L 2/10 422/186.3 |
| 2003/0188740 A1 * | 10/2003 | Tribelsky | C02F 9/00 128/200.14 |
| 2004/0120846 A1 | 6/2004 | Bates et al. | |
| 2004/0120850 A1 | 6/2004 | Kaiser | |
| 2004/0166018 A1 | 8/2004 | Clark et al. | |
| 2004/0238344 A1 * | 12/2004 | Benoit | A61L 9/20 204/157.3 |
| 2005/0118078 A1 * | 6/2005 | Dobbs | B01D 53/885 422/186.3 |
| 2005/0173652 A1 * | 8/2005 | Ressler | A23B 4/015 250/455.11 |
| 2005/0186108 A1 | 8/2005 | Fields | |
| 2005/0205206 A1 * | 9/2005 | Lembersky | A61L 2/0011 156/345.5 |
| 2006/0188835 A1 | 8/2006 | Nagel et al. | |
| 2007/0045561 A1 | 3/2007 | Cooper | |
| 2007/0102280 A1 | 5/2007 | Hunter et al. | |

FOREIGN PATENT DOCUMENTS

| | | | |
|---|---|---|---|
| CN | 2662909 Y | 12/2004 | |
| IL | WO 2004011038 A1 * | 2/2004 | A23B 7/015 |
| JP | 2003207165 | 7/2003 | |
| KR | 20040097758 | 11/2004 | |
| WO | 0023552 | 5/2000 | |
| WO | 0238447 | 5/2002 | |
| WO | 0245756 | 6/2002 | |
| WO | 02078754 | 10/2002 | |
| WO | 2005/061396 A1 | 7/2005 | |

* cited by examiner

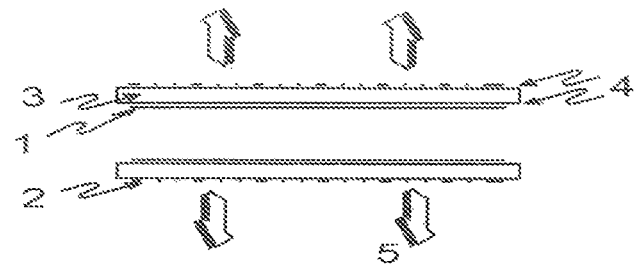
a. NUV Lamp
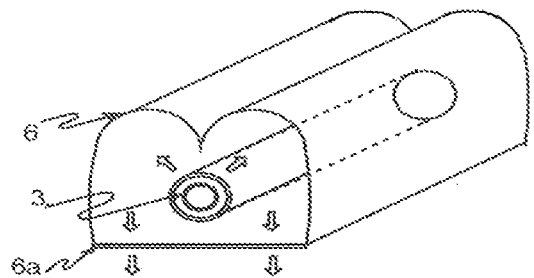
b. Directed Radiation
Figure 1: NUV Source
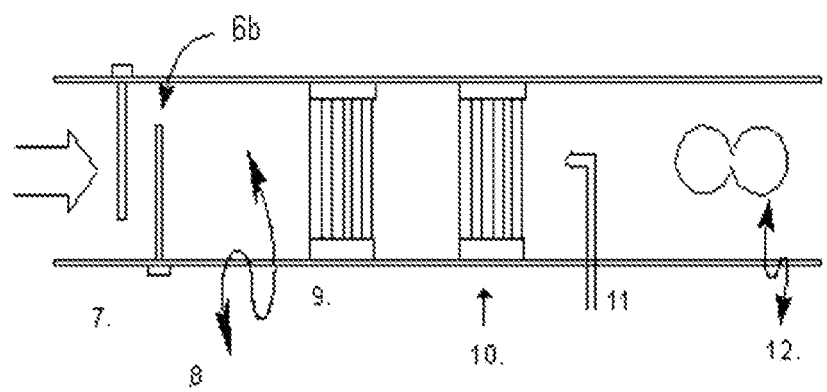
Figure 2: Volumetric Air Treatment

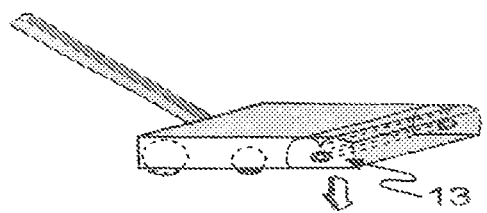
a. floor Treatment & Cleaner
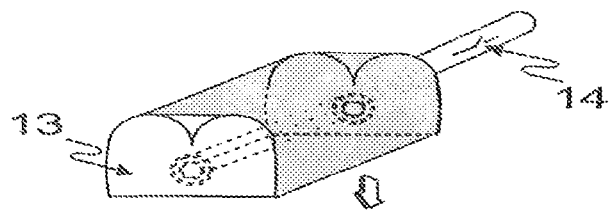
b. Handheld Surface Treatment
Figure 3: Surface Treatment
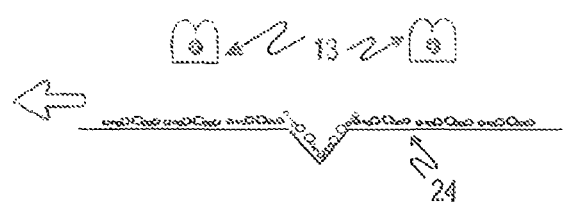
a. Unprepared Food
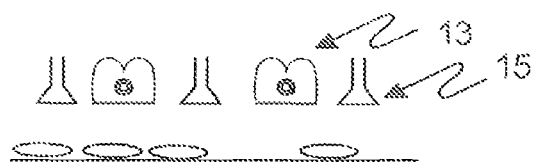
b. Serving Counter
Figure 4: Food Treatment

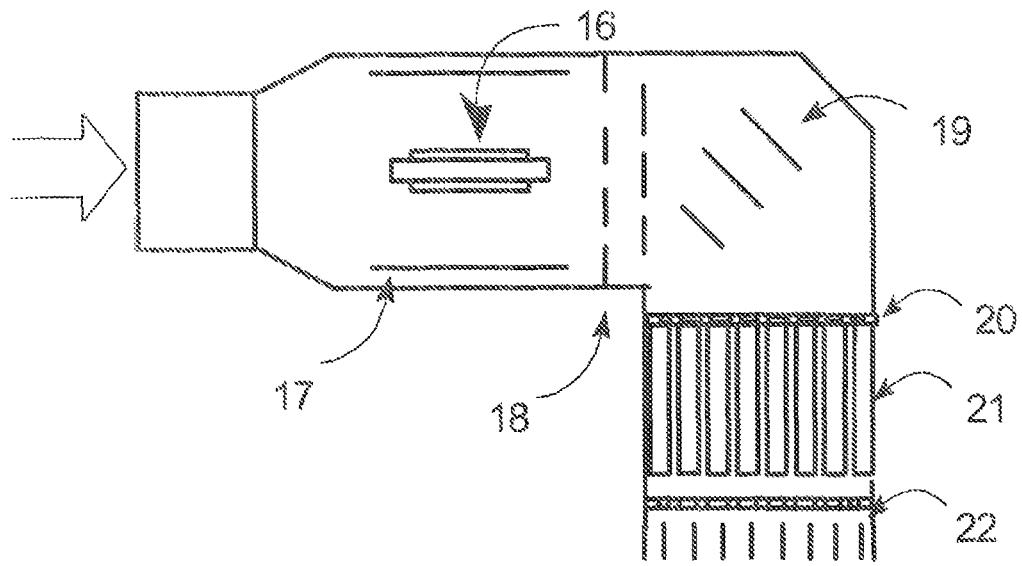
Figure 5: Zone Air Purifier & Sterilizer
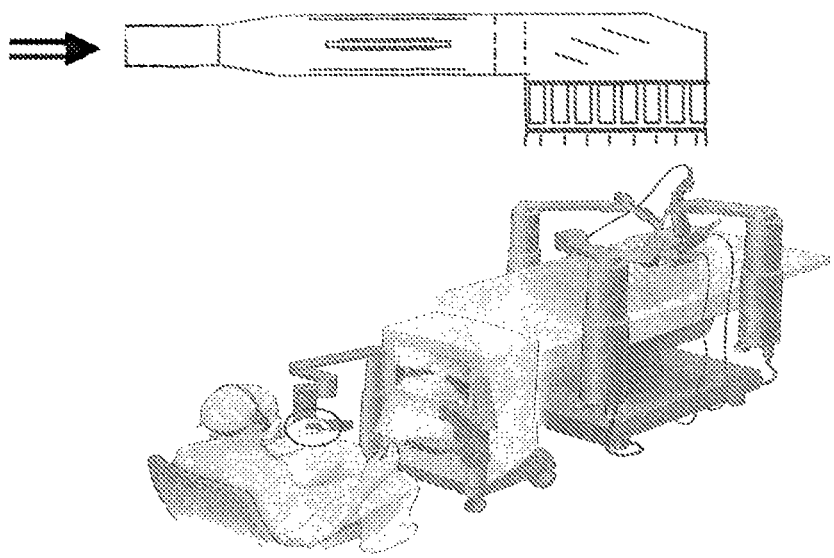
Figure 6: Operating Zone with Sterilizer

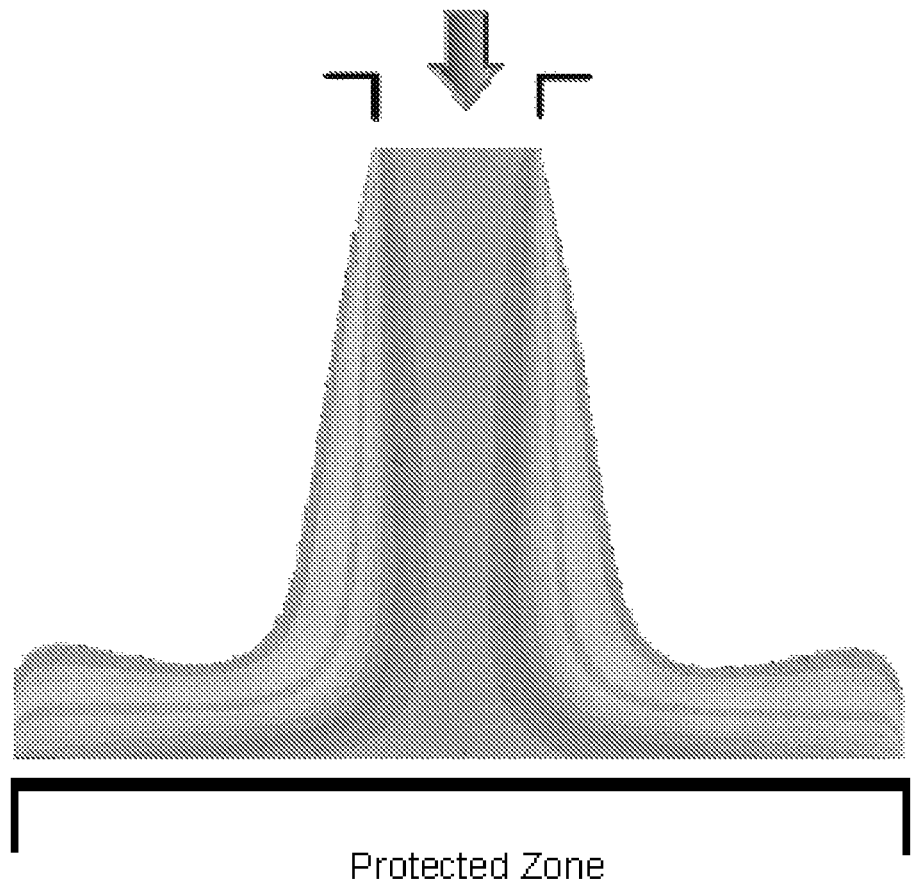
Figure 7: CFD Air Flow

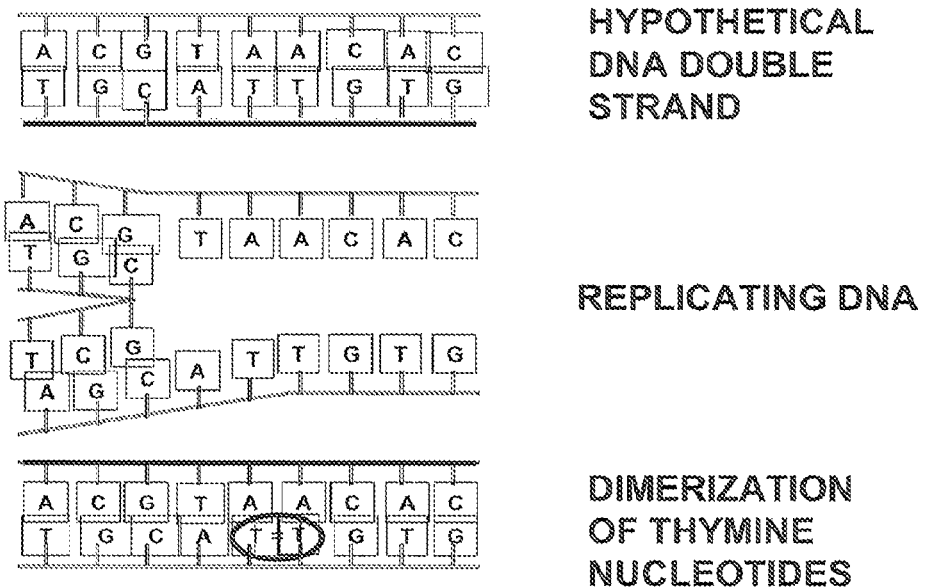
Figure 8: Dimer Formation by UV Photon
(by permission of ERG @ UNH)
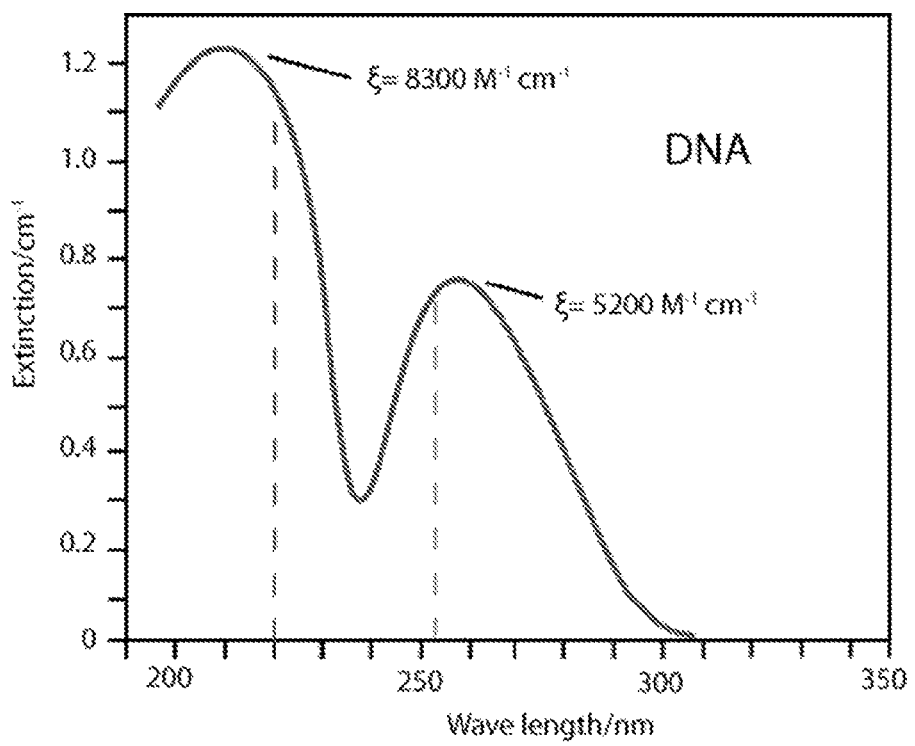
Figure 9: UV Absorption of DNA

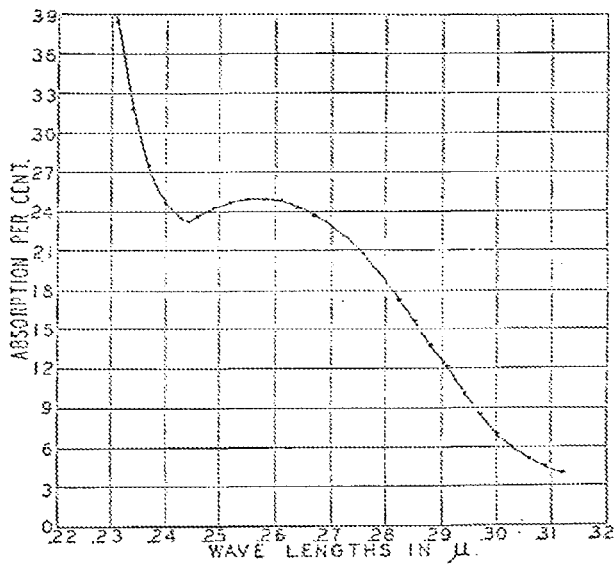
Figure 10: B. coli @ 0.8u absorption
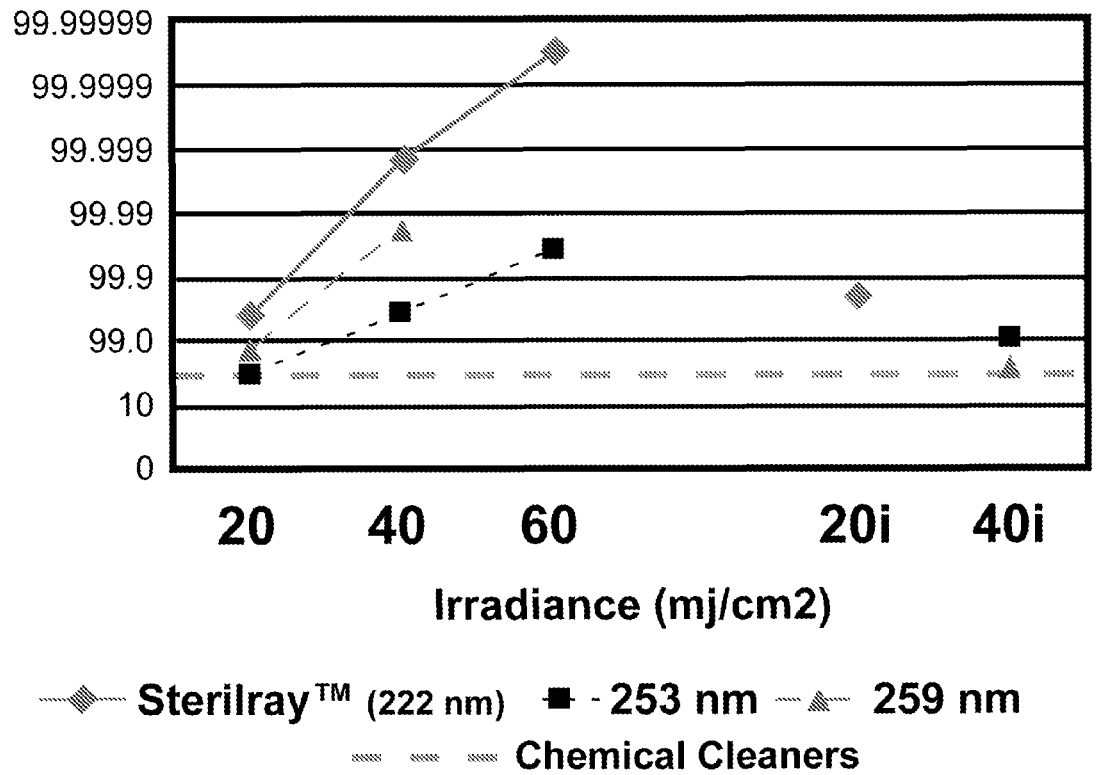
Figure 11: UV Irradiation Test on MS2

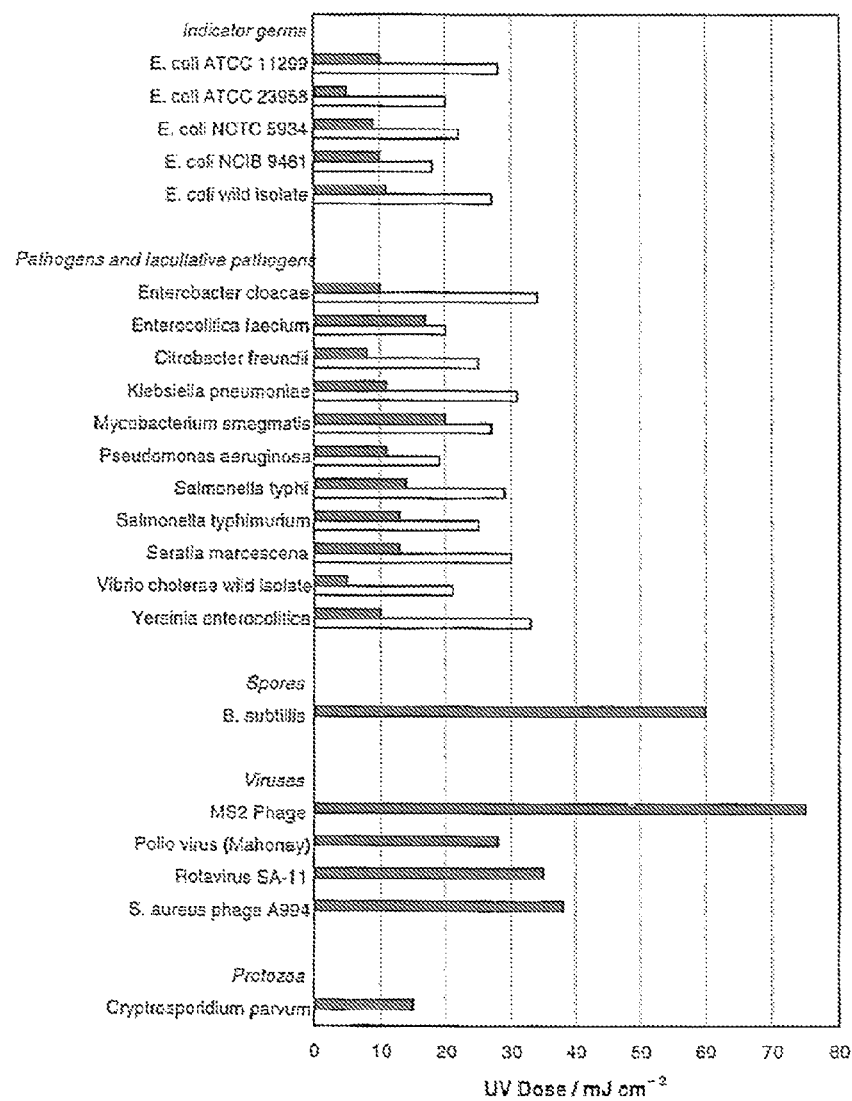
Figure 12: UV dose required for 4 log (99.99%) deactivation

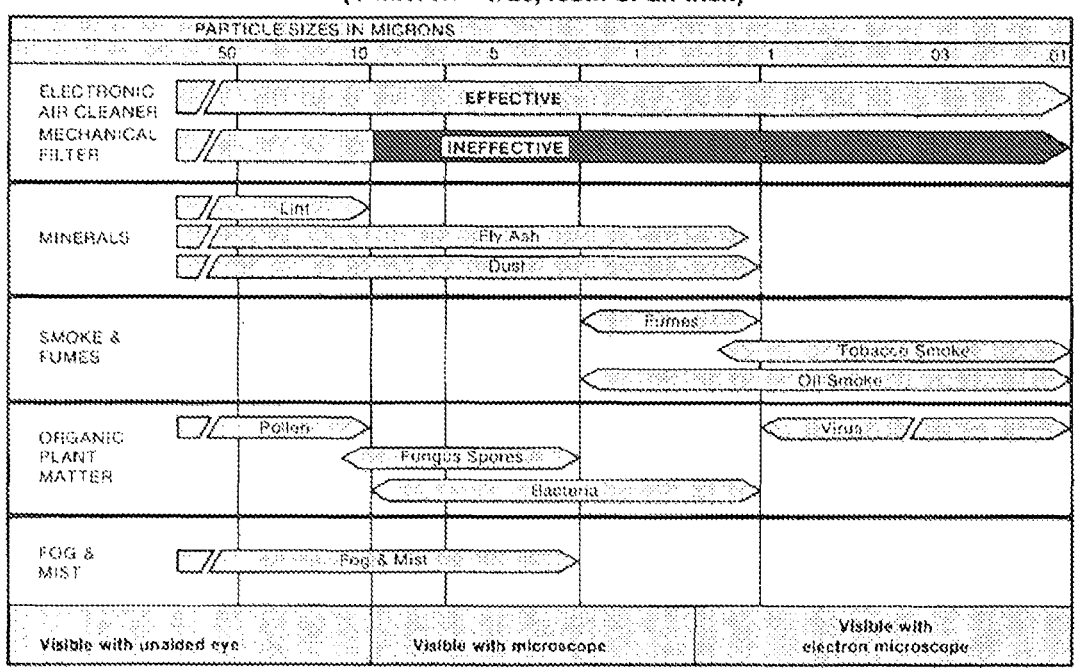
Figure 13: ESP range of effectiveness

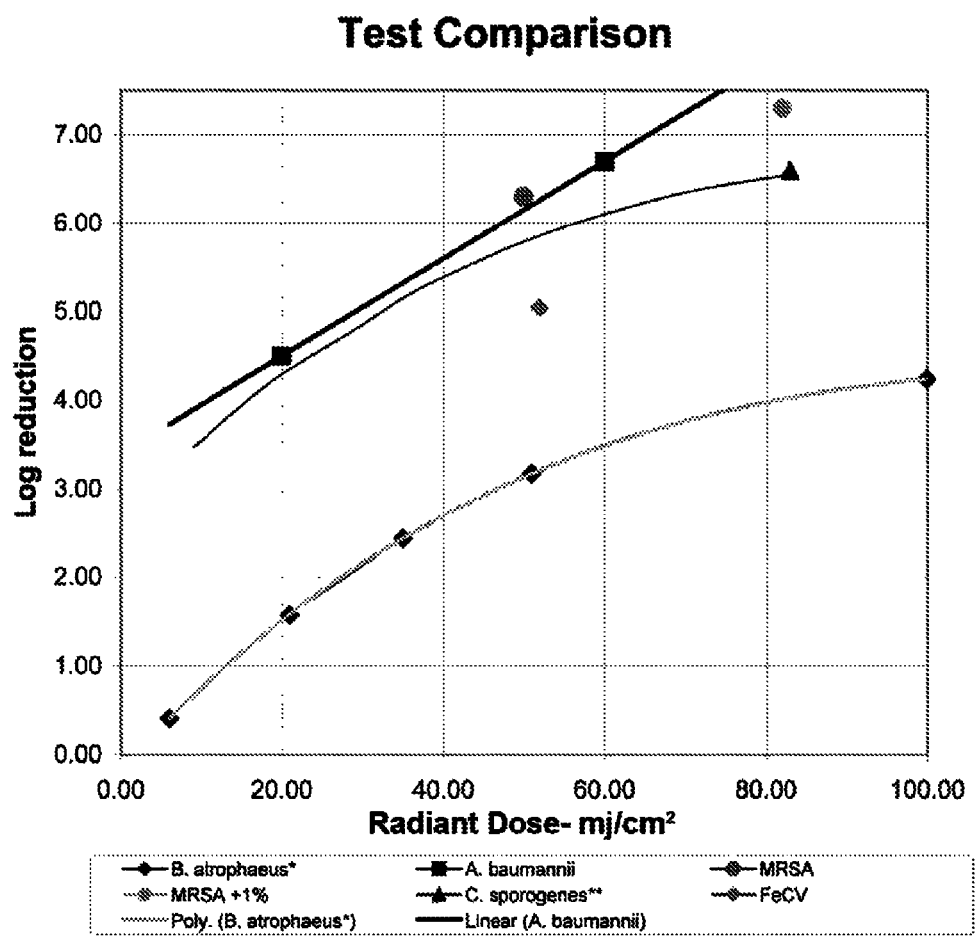
Figure 14: Sterilray Technology Test Data

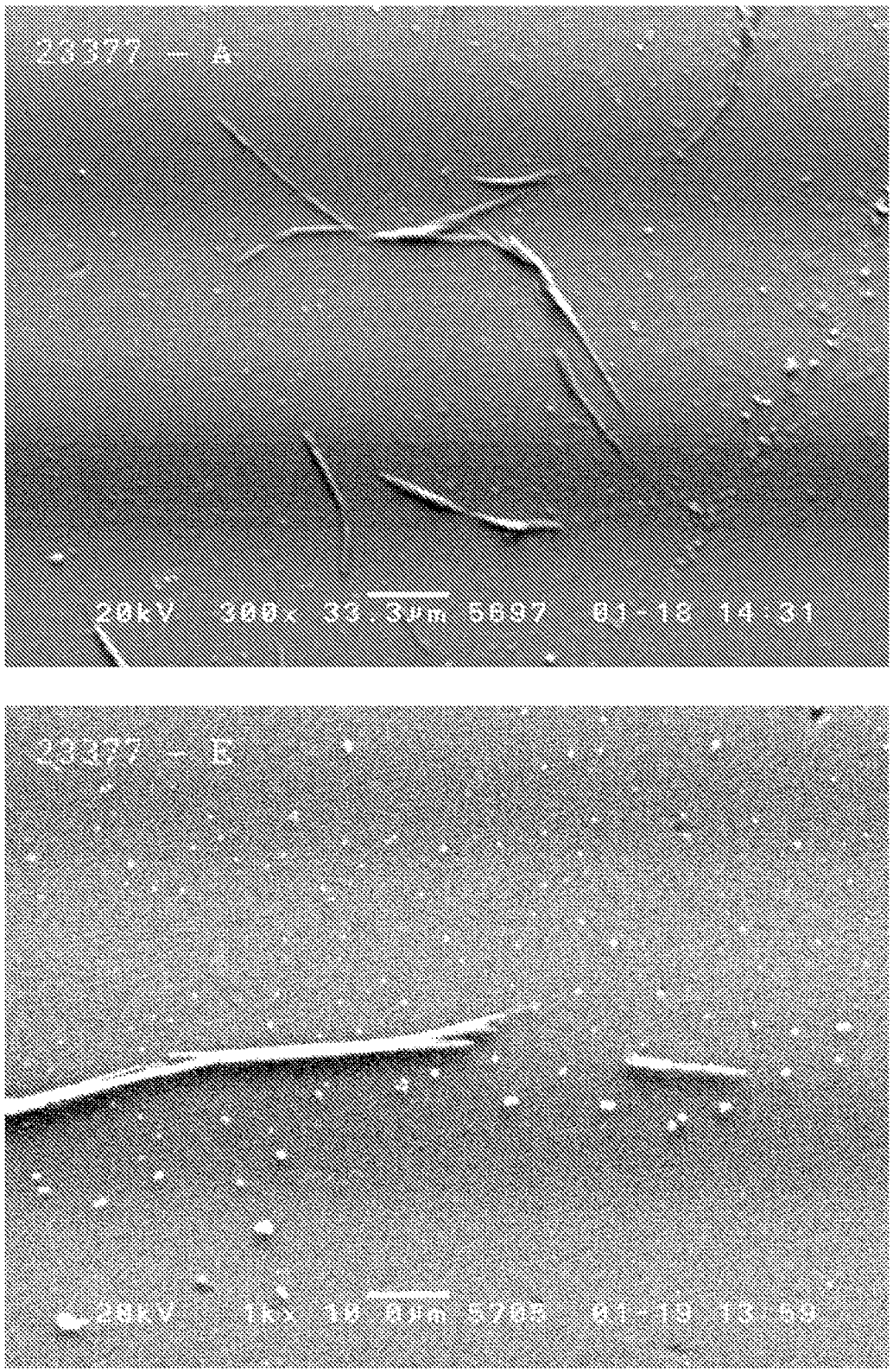
Figure 15: 300x and 100x micrographs of Bacillus atrophaeus

METHOD AND APPARATUS FOR STERILIZING AND DISINFECTING AIR AND SURFACES AND PROTECTING A ZONE FROM EXTERNAL MICROBIAL CONTAMINATION

PRIORITY CLAIM

This application is a continuation-in-part patent application which claims the benefit to and priority from currently pending non-provisional U.S. utility patent application Ser. No. 11/831,667 filed on Jul. 31, 2007, which is a continuation-in-part patent application of International patent application number PCT/US2006/003393 filed on Jan. 31, 2006, currently expired, which is a non-provisional application of U.S. provisional application No. 60/593,626 filed on Jan. 31, 2005.

BACKGROUND

1. Field of the Invention

This specification teaches a new method for disinfecting and sterilizing air, surfaces of all types and food from microorganisms and toxic chemical substances. In addition, it relates to a process and apparatus for protecting surfaces in closed or captured environments (zones) from external sources of microbial contamination in an efficient and cost effective process. These zones can be large volumes such as high rise building, cruise ships and jet airliners, or small volumes such as small rooms or surgical operation areas whether in a hospital operating room or on the battle field.

2. Description of the Related Art

All prior art for sterilizing and disinfecting air has been based on using commercially available ultra-violet (UV) lamps or by using magnetic fields. These lamps are either pulsed or continuous. Continuous lamps are mercury based and emit principally at 254 nm. A number of companies are presently producing UV light based apparatus for the destruction of "virus, bacteria, spores and pathogens" (microorganisms or VSP) that are in room air. This is an effective treatment because it continually exposes room air currents to the treatment light and over time has sufficient exposure time to treat VSP's. The required exposure times range from 10's to 100's of seconds, depending on the light absorption capability of the different virus and bacteria at the 254 nm. While this is effective for treating the room air of individual rooms, it requires a long time to be effective in treating large flowing volumes of air that pass quickly down large ducts. Its long treatment time is impractical for treating most surfaces.

Magnetic based apparatus also require time to deactivate or destroy these VSP's. Two such inventions are directed to specific applications. Wesley, U.S. Pat. No. 4,458,153 is directed specifically towards liquid like substances enclosed in pipes, but does not discuss any test results. Sangster, U.S. Pat. No. 5,750,072 requires an injection of a sterilizing fluid as a mist or vapor for the magnetic field to produce radicals that in turn are used to alter the VSP's. He does not discuss any test results. Hofmann, U.S. Pat. No. 4,524,079 is directed specifically to treating food stuffs. He speaks of requiring up to 100 pulses at frequencies ranging from 5 to 500 kHz. Although the action time would be short, the power required to treat large areas and the apparatus design limit its practical application. None of these patents are admitted to being prior art by their mention in this background section.

The broad ultraviolet spectrum had been divided into three regions depending on its different effects on human skin. Reference to these regions are predominantly made in medical terminology with UV-A defined as a range or band between 320 nm and 400 nm, UV-B defined as a band between 280 nm and 320 nm, and UV-C defined as encompassing wavelengths shorter than 280 nm. Recently the UV-C band has been shortened because strong water absorption causes different effects on the skin below 235 nm. UV-C is now considered the band encompassing wavelengths from 280 nm to 235 nm. The Far UV begins at 235 nm and encompasses wavelengths to the beginning of vacuum UV at 185 nm. Photochemists and photobiologists do not generally use these terms because absorption spectra of chemical bonds are much narrower than these generally defined bands. Instead, they use the wavelength of the applied radiation to define the observed effects.

Claims have been made that UV-C radiation is used to alter the DNA. This is because the mercury lamp emission at 254 nm is close to a good DNA absorption band and is the most widely available UV-C radiation source. None of these claims make reference to any shorter wavelengths and to the absorption band that peaks at 200 nm (see FIG. 9). Most literature credits this peak to protein absorption whereas the peak centered near 260 nm is attributed to many amino acids. In fact, all literature directs researchers away from using any shorter wavelengths due to the high absorption of molecular water. Mercury lamps are used for wastewater treatment and work well for this application. However, this specification teaches that since we do not live underwater, the protein absorption band offers much more significant action spectra that can be used to alter the DNA of microorganisms more effectively. A source of Far UV photons targets this protein absorption band. This concept is a significant advancement and a step change in the technology used for sterilization and disinfection.

During the past few years, new UV emitting lamps based on the excitation of excimers are becoming commercially available. These emitters produce single line or narrow spectral emission at a wavelength determined by the gas composition of the lamp. If the treatment lamp's wavelength is chosen to match closely to the peak of protein absorption of the microorganism's DNA, then a lethal dosage can be delivered to the VSP's in a shorter time. No patent has been found that teaches the use of "new ultra-violet" (NUV) sources coupled with supporting equipment that can effectively and efficiently disinfect and sterilize large volumes of air, large and small surfaces, and food stuffs in various stages of preparation in a practical manner.

The NUV lamp is a coaxial design that can be made as small as a pencil to as large as 1 meter long. Lamp efficiency is about 10-25% wall power to UV emission. The design has several advantages over mercury lamps. Most important is that its gas can be chosen to maximize its emission to the absorption peak of the targeted biochemical. Unlike the mercury lamp, the UV intensity can be varied from near zero to maximum. It will produce 10 to 1000 times more intensity than mercury, depending on the lamp dimensions, and it does not use mercury that will soon become regulated by the EPA.

In this specification, sterilization or sterilize refers to sterilization or high level disinfectant as defined by US FDA. The terms disinfectant and disinfection refers to all other levels of disinfection.

SUMMARY OF THE INVENTION

Destruction of pathogens is significantly improved by targeting a biochemical in its DNA/RNA with the proper wavelength so the critical dosage can be delivered in the shortest time. The concept is to direct the correct spectral emission to target specific bonds with sufficient intensity to destroy pathogens quickly and effectively on all types of surfaces and in the air.

Critical to this apparatus is the development of a new ultra-violet (NUV) source that emits a highly intense narrow wavelength band of photons that correspond to the maximum absorption band for DNA proteins and other component bonds. The preferred embodiment is the NUV source at 222 nm targets these proteins and their peptide bonds.

The NUV source can also be made to emit photons at 282 nm to target a mixture of amino acids and some proteins that absorb at this longer wavelength. For some specific cases, the NUV source may also produce 254 nm photons so as to target specific amino acids. The process is to use the irradiance from the NUV apparatus to produce high levels of disinfection on all types of contaminated surfaces and air and to destroy Biotoxins and nerve agents. The process includes support apparatus, ozone with the NUV source and preconditioning liquids and sprays that affect the tightness of the polypeptide helix which may improve absorption by the pathogen proteins or amino acids that result in improved destruction at lower dose or less time or both.

Background for NUV Apparatus

The genetic makeup of all living organisms is contained in their DNA molecule. This is a nucleic acid molecule that contains the genetic instructions to construct other components of living cells, proteins and RNA molecules. Replication occurs by the splitting of the DNA molecule, which duplicates itself through a transformation of its structure. Parts of the DNA molecule have been given names such as pyrimidine bases, cytosine, thymine or uracil that form a group of biochemicals that sustain life. The long DNA molecule holds itself together by using simple bonds like those found in sugars.

Researchers believe that the energy of the UV photon causes the formation of a strong (covalent) bond to develop between specific biochemicals. However, the bond strength of the covalent bond is very dependent on the relative position of the participating atoms. When the bond is symmetrical on both sides of a hydrogen atom in the bond, it is referred to as a dimer. A dimer is a very strong bond and is not generally broken during the vaporization of the liquid. UV light is known to produce Thymine, cytosine-thymine, and cytosine dimers. After the formation of the dimer, further replication of the DNA stops. FIG. 8 shows the concept of the dimer formation in a DNA molecule.

The DNA molecule absorbs light from about 180 nm to about 300 nm. One of the most effective wavelengths to treat VSP's in water is about 254 nm because of low water absorption. However, water absorption of UV light increases steadily as the wavelength decreases below 240 nm. This limits the ability for UV light of shorter wavelengths to be as effective for water treatment.

A standard commercial light source for UV irradiation near the 260 nm absorption peak of DNA is being produced by using mercury as the source for generating photons. The mercury gas and its pressure in the lamp determine the wavelength of the emitting light. For low-pressure (LP) and low-pressure high output (LPHO) lamps, the emitting wavelength is near 254 nm. For medium pressure lamps, the emission ranges from 200 nm to above 300 nm. However, the strength of the emitted light is not effective below 245 nm for the continuous emitting lamps and below 235 nm for medium pressure lamps. Xenon gas in pulsed lamps produces a similar emission as the medium pressure mercury lamps.

DNA action spectra show that absorption increases as the wavelength decreases, with a relative maxima at 260 nm and largest at 200 nm. Many articles indicate the principal action spectra of the DNA absorption is from 245 to 280 nm range and do not address the 200 nm peak. An exception is FIG. 9 which graphically shows this relationship (Von Sonntag; Disinfection by free radicals and UV-radiation. Water Supply 4, 11-18 (1986)). Since water absorption significantly increases below 240 nm, it becomes apparent that DNA effectiveness curves that omit the 200 nm peak apply only to organisms in water.

MS-2 Phage is a marker virus that is used to measure reproduction viability after UV irradiation. FIG. 10 is DNA absorption without the influence of water (Gates, F. L. A study of the bactericidal action of ultra violet light III. Jour. General Physiology 14, 31-42 (1930)). Absorption is more than doubled at 220 nm.

A recent technical paper (Peak et al, UV action spectra for DNA dimer induction; Photochemistry and Photobiology, 40, 5 (613-620)-1984) suggests that dimer formation is not the only requirement to inactivate DNA. Absorption of other molecular groups in the long DNA chain increase as the wavelength is reduced from 254 nm. Damaging or destroying these bonds may be more effective in deactivating the DNA than compared to the 254 nm band. Reports show that damage caused by 254 nm light can be reversed by longer wavelength UV and blue light (FIG. 12). The DNA of pathogens not expected to have this 'photo-reactivation' phenomenon after being exposed to higher energy 222 nm photons.

The energy of the emitted photon is determined by its wavelength. Photon energy is about 5 ev at 250 nm, and increases for shorter wavelengths. Different bonds in the DNA will be affected with photons of different energy.

The 540 kJ/mole photon energy from the NUV lamp exceeds the bond energies of many of the peptide bonds. This should cause physical damage to the microorganism. FIG. 15 shows a micrograph of the *Bacillus atrophaeus* after receiving a radiant dose from a NUV lamp. It shows a magnification of 300× and 1000× taken at low power to prevent any physical damage to the organisms during the picture process. The results of photon impact can be clearly seen in the 1000× frame by the ruptured sidewalls and segmentation of the organism. This is the first indication the author has seen that photons are actually causing physical damage and destruction to pathogens. A corresponding slide that received the same radiant exposure confirmed that all organisms were dead.

A NUV lamp emitting at 222 nm is considered the most effective source because DNA molecules and biochemical's have greater absorption at this wavelength. The steep rise in absorption below 240 nm is exhibited by most proteins. It has been fairly well established that the peptide bonds in protein molecules are responsible for the steep rise in absorption. This occurs as well for nucleo-proteins, aromatic amino-acids, diglycine, triglycine, and bovine albumin (McLaren, et al, Photochemistry of Proteins and Nucleic Acids, Pergamon Press, Macmillan Company, 1964). An organic chemist suggests that this lower wavelength is more effective in breaking bonds and producing dimers in the purine bases and sugar phosphates instead of the pyrimidines.

This wavelength is not strongly absorbed by water vapor and oxygen in the air. However, at 200 nm, oxygen absorption increases by 10 times and water absorption becomes slightly greater than oxygen. At 200 nm, ozone production vs. irradiance can not be controlled as it can at 222 nm. This would create a large amount of ozone that is harmful to humans and animals and reduce its effectiveness for applications in air, particularly for long irradiation distances.

Tests

Using a lamp that emits 222 nm, a comparison test with and without water was made to determine the effect of this radiation on organisms. The organism used in all tests was the MS-2 virus, which has become a standard indicator of mutation effectiveness. The EPA report (811-R-96-002) reports a 4.3 average log reduction of the MS-2 virus using mercury light 254 nm at an irradiance greater than 128 $mj/cm^2$.

Three wavelengths were tested: 222, 253, 259 nm. The 222 nm lamp was tested at three levels of irradiance with the virus in a thin layer of water in order to reduce the absorption effect of water. A separate test was also done with the virus in more water. The 253 and 259 nm lamps were tested at the identical irradiance levels with the virus in water. Controls were made on all tests and a single test dish on each lamp was made to check experimental error.

The 222 nm lamp (FIG. 11) produced log 5 reductions at 40 $mj/cm^2$ and log 6.5 reductions at 60 $mj/cm^2$. The water test produced a 3.2 log reduction, which matched the equivalent calculated irradiance in air. The 253 and 259 nm lamps produced about log 4 reductions at 60 $mj/cm^2$. A 3 million reduction in population is about 10 to 100 times more effective than reported mercury 254 nm results at the same irradiance.

The results of the test indicate that 222 nm light is very effective in causing mutations and destruction in microorganisms. These tests indicate an improvement of between 10 to 1000 times, depending on the intensity of the lamp. It is important to note the improvement of the 259 nm source compared to the 254 nm source. This produced a 10 times improvement in the test sample for just a 5% increase in absorption. It illustrates the importance in using a UV photon emitter that is near the absorption peak of the DNA or targeted chemical such as proteins, nucleic acids, or amino-acids.

FIG. 12 illustrates the 254 nm dose required to deactivation different VSP's. The bars represent with (solid) and without (open) photo-reactivation. Note that a dose of 75 $mj/cm^2$ is required to deactivate the MS2 Phage virus and prevent photo-reactivation. In the tests shown in FIG. 11, half the dose at 222 nm was just as effective as the higher dose at 254 nm. Even though the sample was under water, the 222 nm radiation was still more effective than 254 nm radiation.

The 222 nm photon has more energy and is absorbed by S—N, S—O, O—O, O—H, and many carbon bonds that do not absorb 254 nm. This suggest that 222 nm light may also prevent DNA repair that has been reported when low level 254 nm UV sources were used.

FIG. 14 presents further testing done in independent research laboratories on many different pathogens. They include spores Bacillus atrophaeus and Clostridium sporogenes, feline calici virus, bacteria Acinetobacter baumannii, MRSA, MRSA+1% serum. The chart plots radiant dose against a log reduction of the target microorganism. It shows that high log reductions were achieved for viruses, bacteria and spores. This chart presents data that does not determine the minimum dose but only the log reduction at the dose tested. Since many tests represented a 100% kill, a lower dose could obtain the same log reduction at or near 100% kill.

A survival plot was made of the Bacillus atrophaeus spore. Since it is known to be one of the most difficult spores to kill or deactivate, this curve represents the base line for the dose required to kill most pathogens for the NUV source. Future tests will generate survival plots of the other pathogens to determine the minimum dose for various log reductions.

Since the NUV source can produce an irradiance of 100 $mw/cm^2$, then a log 4 reduction of all but the B. atrophaeus can occur in a 0.1 second treatment resulting in a radiant dose of 10 $mj/cm^2$. The chart demonstrates that the NUV source is a potent sporicide as well as capable of producing high disinfection on VSP's.

Technical Discussion

Critical to the destruction of the organism is targeting the proper biochemical with the proper wavelength so the critical dosage can be delivered in the shortest time. The critical dosage is that dosage that destroys or deactivates the organism and prevents its replication.

Pyrimidine and purine bases of nucleic acids have a strong absorption near 260 nm. But proteins also have an absorption maximum at about 280 nm due to the absorption by the aromatic amino acids phenylalanine, tyrosine and tryptophane. Numerous lipids also absorb near this peak. They include indole acetic acid and Lipase. And there are some major differences that occur in the synthesis of DNA to RNA. The protein thymine is replaced by the pyrimidine base uracil that has absorption near the 280 nm and not at lower wavelengths.

It is important to note that biochemicals of DNA and RNA will have different absorption spectra and the peak absorption will be shifted by water, pH, temperature, previously absorbed light and surrounding contaminates in the air. Uracil and cytosine are particularly susceptible to photohydrate formation. A protein crosslink can be formed between a pyrimidines base and an amino acid. Cysteine and thymine are easily affected and uracil preferentially binds to cysteine, phenylalanine and tyrosine. Protein crosslinks induce irreversible cell damage. The disulfide group of cysteine can be split into reactive sulfhydryl groups. Tryptophane (280 nm absorption) can provide the singlet energy transfer to split the disulfide groups that strongly influence the structure and function of proteins in the DNA/RNA complexes.

The presence of ozone can significantly induce damage to the long polypeptide amino acid chains and shorten the UV action kill time. For some applications, the NUV intensity is increased to produce some ozone to improve the pathogen destruction of the contaminated surface.

Test data confirmed that proteins in the RNA of the norovirus do not absorb the NUV wavelength at 222 nm effectively. However, a number of RNA proteins do exhibit strong absorption near the amino acid peak absorption of 280 nm. More likely is the fact that RNA absorption is due to the combination of the proteins and the locations and types of amino acid bonds surrounding them. Testing is underway to confirm that a NUV source at 282 nm will cause similar destruction to the RNA of the norovirus compared to the DNA destruction seen in FIG. 14.

There are many UV absorption plots that indicate how the degree of absorption in the DNA/RNA molecule changes with wavelength as the pH of the carrier solution is changed. The secondary structure is a term used to describe the coiling of the polypeptide chain. The tightness of the coil is also significantly affected by pH of the solution. This suggests that the closeness of the different amino acids to peptide bonds affect the DNA/RNA absorption at a specific wavelength. Consequently, pre-treating the surface with a solution or spray that improves the absorption of the targeted proteins and amino acids prior to delivering a UV radiant dose is also being tested. In many cases, it may significantly improve the process by reducing the UV dose or treatment time. The concept of using the NUV source in conjunction with wipes and liquids for treating VSP's on surfaces is also contained in the scope of this specification.

Biotoxins and nerve agents can be used by terrorists as weapons against groups of people. Nothing economical has been developed that could mitigate an attack and prevent the loss of life and incapacitation at the point of attack. While government agencies of the US have developed detectors that could be used in the future to warn people in the confined areas that are under attack, nothing would prevent the attack from being effective.

Biotoxins and nerve agents are organic molecules that contain either DNA or have long chain carbon molecules. Both of these are susceptible to destruction using NUV light sources. 222 nm will destroy the C=C and C=O bonds causing the destruction of the chemical. Future testing will determine if the molecular extinction coefficient is sufficient to make this effective means for their destruction.

The most effective means for delivery of these agents is to spread them in a gas phase through the air ventilation system. A detector would be used to turn on sufficient NUV sources so that the agents are destroyed before exiting the ventilation system into the confined area where the captured population is present. Tests still need to be done in regulated and controlled laboratories to develop the criteria for these sources to be effective and become the first line of defense.

The use of a high E field electrostatic precipitator (ESP) is important to the sterilization and disinfecting apparatus for air in some situations. FIG. 13 compares the range of effectiveness with mechanical filters for different pollutant sizes. As illustrated in the fourth column, it is capable of removing some percentage of VSP's. However, since it can also capture fog and mist, it has the ability to breakdown ozone $O_3$ into oxygen. Its use prevents levels of ozone from exceeding the EPA exposure safe levels.

In some cases the air disinfecting apparatus includes a humidification system to provide and maintain minimum moisture content at predetermined and controllable levels. In addition, the apparatus contains baffles and zone restriction devices that enhance the zone protection and minimize the positive pressure required to maintain the protected zone.

The concept of using the NUV source with associated support equipment for air disinfection of VSP's is valid and is also contained in the scope of this specification.

Apparatus and Process Discussion

The NUV source apparatus is made to supply a narrow emission band of UV light that is close to the peak absorption of the targeted organism or chemical with sufficient photon energy that break bonds. Unique to obtaining short action (kill) times is a determination of the specific wavelength required to destroy the targeted organism or chemical.

The process is to direct the correct spectral emission to target specific bonds in proteins and amino acids in the DNA/RNA molecule with sufficient intensity to destroy pathogens quickly and effectively. It is effective for the breakdown of biofilm and protein based allergens.

The preferred embodiment is a NUV source at 222 nm. This spectral emission is $10^4$ times more effective than standard mercury based lamp UV light for altering the DNA. Action times are reduced from 10's to 100's of seconds to times less than 0.1 seconds.

The NUV source can also be made to emit photons at 282 nm to target a mixture of amino acids and some proteins that absorb at this longer wavelength. This may be particularly important for single or double strand RNA of influenza or noroviruses. For some cases, the NUV source may also produce 254 nm photons so as to target specific amino acids. And the photon energy of the NUV source is sufficiently high to break carbon bonds of chemical toxic substances or biotoxins with similar action times.

This invention uses the NUV source that makes it cost effective in treating surfaces of materials since the action time is very quick. The apparatus of this invention is designed to make direct photons to the intended target as effectively and efficiently as possible. This makes for a cost effective process for sterilizing and disinfecting air, all types of surfaces and food during normal daily activity and prevents the previous need to restrict occupation and use of areas being treated.

Surfaces

The apparatus is designed to quickly disinfect floors, hand rails, objects that are in constant contact with transient populations for the purpose of preventing transmission of disease and toxic substances that can cause injury or illness to these populations. As a hand wand, it only needs to be waved or passed over the surface to obtain a high level of disinfection.

The NUV radiation can be applied to any object or surface that needs to be disinfected and/or sterilized. An example would be the use of a caddie cart whereby all instruments, papers and pens would be exposed after a patient examination to prevent the transmission of pathogens to the next patient. The cart could also provide a means to disinfect protective gloves or face masks if a shortage occurs during a pandemic. Testing will determine the correct exposure limits to prevent any harmful effects that could occur when used to disinfect human skin, hands, animal surfaces such as skin, fur, and hair, and critical plastics and materials used in medical devices. It also has the potential to sterilize/disinfect medical equipment and surfaces and critical parts on an industrial assembly line prior to packaging.

In one specific embodiment of use, the present invention may be applied to skin disinfection. The wavelengths contemplated herein are not damaging to the epidermis, and therefore can quickly and effectively disinfect human or animal skin without skin cell damage. In one example, a doctor or nurse may expose their hands to the NUV source before, during, and/or after surgery. Because the NUV source may disinfect in a fraction of a second, hand disinfection is very quick and convenient, and can be done repeatedly to prevent any spread or growth of micro-organisms. Other examples of skin disinfection may be applied to livestock industries, food processing and treatment industries, pet cleaning, and the like. Livestock may be exposed to the NUV source to keep them clean and disinfected and prevent infection or spread of infection. Similarly, food treatment and processing industries may use the NUV source to treat and disinfect skin of animals and/or animal carcasses, as well as exterior surfaces of food products such as eggs, fruits and vegetables, leafy greens, eggs, nuts and any food products that need some level of disinfection such as spices, grains, and horticulture such as flowers and plants.

In one embodiment that may be particularly applicable to skin and/or wound (non-skin flesh) disinfection, at least one of 207 nm, 222 nm, or both may be used as wavelengths emitted from the NUV source (or two different NUV sources). These two wavelengths may be emitted by an excimer lamp or lamps. In an embodiment emitting both 207 nm and 222 nm, two separate lamps may be used, the two lamps in close proximity to each other. In another embodiment, a dual annulus lamp may be utilized. This lamp may have three coaxial tubes defining two annuli filled with two different gasses to generate the two wavelengths. Electrodes may serve to excite the gasses, emitting the two wavelengths simultaneously and from a single source.

Because the lamp in this embodiment's wavelength is chosen to match closely to the peak of protein absorption of the microorganism's DNA, both 207 nm and 222 nm may be particularly useful for skin and wound disinfection because they do not penetrate the epidermis, and 207 in particular does not damage human or animal cells. Similarly, 222 nm kills non-epidermis cells entirely, and therefore there is no concern of DNA mutation which leads to diseases such as cancer. As such, these two particular wavelengths are particularly well suited to skin and wound disinfection: Both are useful on skin because they do not penetrate the epidermis; and both are useful on wounds because 207 nm will not damage the exposed flesh, while 222 nm will kill exposed cells, but not cause them to mutate, eliminating radiation concerns. From an effectiveness standpoint however, 222 nm is approximately 3-4 times as effective at disinfection compared to 207 nm. Thus, while 207 nm alone is an option for disinfection, generally 222 nm alone or in combination emission with 207 nm will be utilized for most embodiments.

In another embodiment, the NUV source may be mounted on an automated robot, the robot being programmed and configured to disinfect a room automatically. This robot may be specifically configured to disinfect hospital rooms automatically but moving into the hospital room, and activating the NUV source. This will disinfect all air and surfaces exposed to the UV radiation from the NUV source. Further, the robot may be configured to move around the room to expose other surface and air zones to the UV radiation from the NUV source. It should be understood that this embodiment is not limited to hospital room disinfection, and could be used for any room disinfection with the NUV source attached to a robot or robot controlled device. For example, the robot may be an automated vacuum cleaner or floor cleaner, or a robot specifically configured to enter a room in a building to disinfect the room.

In yet another embodiment, the NUV source can be used to disinfect all types of liquids by passing them through the center of the lamp where coupling efficiency with the light is maximized. Any liquid such as milk that will flow and requires some level of disinfection would be applicable. This would include wine, water for all types of uses, food products from salad dressings with low viscosity to chocolate which is most viscous. Other liquids used for medicines and health care would be disinfected at the point of container filling thereby killing any bacteria that could be resident in the piping and tubing from the supply vessel.

In another embodiment, the NUV source can be used to kill insects and psyllids that are transporting disease or harmful bacteria. As part of the killing process, it can also be used to prevent the spread of these insects by providing a containment area where they are killed if they try to fly through the irradiated zone. For example, the NUV source may be deployed in a field of crops itself, or may be used to set up a containment area around the field of crops. In a further example, containment areas may be set up around areas frequented by humans or animals to prevent infection and/or transfer of disease caused by the insects and/or psyllids.

In another embodiment, the NUV source can be used to kill fungus and molds in the fields of wheat, corn, cotton, and coffee as well as protect any other plants that need to be kept mold or fungus free. It can be further used to break down mycotoxins on food products that are produced by molds and fungus.

In another embodiment, the NUV source can be used to disinfect parts of containers that come in contact with storing food. Examples of these surfaces include bottle caps, the inside of bottles and plastic containers, and the inside of tubing and containers that handle these food products in the manufacturing and transporting in preparation to filling in consumer containers.

Other non-limiting examples of uses for the NUV source may include disinfection on foods of all types, including meat, poultry, eggs, vegetables, fruits, and the like. In particular blueberries and tomatoes may be particularly well suited for such disinfection because of their susceptibility to infection. Moreover, the NUV source may be useful for disinfection of conveyor lines, chiller liquids, water used for production requiring high levels of disinfection, hatcheries, farming, and the like. However, as noted previously, the NUV source contemplated herein may be applied to disinfection of any zone (such as a volume of air), or surface, and is in no way limited to the applications noted herein.

Because the NUV source is a light source, it can be directed to expose different levels of thick and loose materials by using light conducting fibers to distribute the light intensity. An example would have the NUV source disinfecting a floor by directing it at the floor while some of the light is directed to the bottom of a rug or floor scrubbing brush by light fibers imbedded in the brush. In a similar manner, products that have cavities or areas not exposed directly by the external source could be disinfected. An example of this would be a single fiber used to direct NUV light into a tooth cavity to disinfect the walls and tissue inside prior to sealing with a filling.

The NUV source can be used to directly disinfect room surfaces, apparatus, fixtures and clothing or particles and microbes in the room air by directly exposing all objects for the required exposure time. Several sources can be combined to assure exposure to all surfaces and to reduce total exposure time. It can provide effective treatment to isolation room air by preventing pathogens from remaining alive after exiting or entering the room. Rooms contaminated by bioterrorist agents could be treated by moving using robots to move the NUV source(s) in many directions and moving it (them) around the room during treatment.

Food

The NUV source may provide a significant improvement to the disinfection of food stuffs. The apparatus can be designed for each application that includes foodstuffs in conveyor assemblies, stationary carts and in handling routes during the movement from storage to food preparation processes. It can be use to disinfect specific types of foods such as seeds and sprouts prior to planting, raw food stock like fruits and berries and leafy greens as they are prepared for transportation from the fields to processing centers, to warehousing and storage, to supermarket handling and kitchen preparation and delivery to the consumer. Furthermore, the process can be used to disinfect cutting and working surfaces of meat and poultry packaging rooms and even the cutters and equipment used to transport meat, poultry and other food products.

E-beam sources are currently the only other mechanism being tested to protect food supplies. It does irradiate food with high energetic electrons that is now causing concerns by many about the safety of the product after irradiation.

Air

Normal breathable air contains many contaminates including moisture droplets, dust, lint, bacteria, virus, cists, and spores. The NUV apparatus can be used by itself to disinfect air. The short action time means the NUV lamp can destroy pathogens in the air as they pass by. Another important consideration for its use in disinfecting of air is that it does not contain mercury.

Sterilization sometimes requires the removal of all particles to the smallest possible size. The NUV source can produce byproducts that must be removed for some treatment applications. These byproducts include oxidized air (ozone), condensable chemical byproducts, and damaged microorganisms. Critical to the apparatus is the removal of these contaminates and byproducts. In some special applications, ozone is produced by the NUV source to make treatment more effective. Consequently, the apparatus includes the making of ozone, the use of high E field precipitators and other UV light to remove ozone downstream after the disinfection area and apparatus to make effective use of the combination of these technologies.

Sterilized air is then used to prevent microbial contamination of a protected zone by preventing the influx of untreated air from outside this zone. The apparatus includes pressurizing equipment and zone baffles that provide sufficient outflow from the protected zone so as no contamination can occur. Protected zones can be as small as a wound area on a battlefield operating table to a cruise ship, airplane, or high rise building with thousands of inhabitants.

BRIEF DESCRIPTION OF DRAWINGS

FIG. 1 is a perspective schematic view of a preferred embodiment of the present invention defining the location of important components of the NUV source therein.

FIG. 2 is a perspective schematic view of a preferred embodiment of the present invention defining the location of important components for disinfecting or sterilizing large volumes of air therein FIG. 3 is a perspective schematic view of a preferred embodiment of the present invention defining the location of important components for disinfecting floor surfaces and other surfaces such as chairs, hand rails, counter tops, trays, table tops and the like therein.

FIG. 4 is a perspective schematic view of a preferred embodiment of the present invention defining the location of important components for disinfecting food prior to handling by kitchen or cooks before serving therein.

FIG. 5 is a perspective schematic view of a preferred embodiment of the present invention defining the location of important components for sterilizing air that is used to cover and protect the zone around a surgical operation or procedure independent of the location of the operation therein.

FIG. 6 is a perspective schematic view of a preferred embodiment of the present invention illustrating the zone air sterilization apparatus in conjunction with the remote protected operation zone therein.

FIG. 7 is a CFD view of a preferred embodiment of the present invention defining the emitted airflow pattern from the sterilization apparatus that is used to cover and protect the zone around a surgical operation or procedure independent of the location of the operation therein.

FIG. 8 is a graphic showing dimer formation in a DNA molecule.

FIG. 9 is a graph plotting UV absorption of DNA according to wavelength.

FIG. 10 is a graph plotting DNA absorption without the influence of water.

FIG. 11 plots the effectiveness for reduction of the MS-2 phage virus by different wavelengths of UV radiation.

FIG. 12 plots the UV dose required to achieve a four log deactivation of selected microbes using 254 nm UV light.

FIG. 13 is a graphic comparing the range of effectiveness of various filters for removing airborne particles.

FIG. 14 is a graph comparing tests of different pathogens for log reduction for different radiant dosages of NUV light.

FIG. 15 is a low power exposure at 300× and 1000× micrographs of the *Bacillus atrophaeus* organism after receiving a radiant dose from the NUV light source.

DESCRIPTION OF THE PREFERRED EMBODIMENTS

The drawings illustrate the invention in its different forms and the apparatus required for sterilization or disinfection of air and surfaces that contain VSP's. FIG. 1 illustrates the NUV light source. FIG. 1a shows the NUV source. The high voltage electrode 1 is located inside the inner tube of the annular lamp. The ground electrode screen 2 is located on the outside of the annular lamp. The gas that produces the UV photons is located in the annular region 3 between the inner and outer tubes 4. The gas type is chosen so that the emitted UV photons are absorbed by the targeted microorganism or chemical. The preferred embodiment is 222 nm but could also be 282 nm. UV radiation is emitted radially outward 5. Changing the voltage or current between the two electrodes changes the amount of UV radiation that is produced.

FIG. 1b illustrates the NUV light source used to direct the UV photons towards a specific location, direction, surface, material or substance. The NUV source is shown in the center of the drawing as an end view. The specialized reflector 6 end view incorporates a specialized 'gull wing' design so that >90% of the emitted light is directed to the planar surface below. The specialized reflector 6 also incorporates barium sulfate ($Ba_2SO_4$) as the reflective material in order to maximize the number of photons that are reflected onto the planar surface. In some cases, a cover 6a is necessary to protect the NUV source and reflector from dirt. This cover is transparent to 222 nm and 282 nm light. The specialized reflector can also have different shapes that change the directed radiation for different applications.

This design provides a convenient method and apparatus to disinfect commonly touched objects that act as fomites to transmit pathogens from one person to the next. It would also provide a means for wound treatment prior and post surgery and for the treatment of chronic wounds. It is also provides a means to disinfect hospital and health care rooms, operating tables, hand rails and equipment surfaces that support patient care.

Furthermore, in cases of critical shortages of gloves, robes and masks, the NUV source can be used in this manner to disinfect periodically when appropriate instead of retrieving new ones from supply.

The NUV source(s) can also be used to disinfect patient examining tools, records, pens and equipment between patients. Everything that is brought into the room for examining the patient should be put through the medical caddie after exiting the room and retrieved only after changing gloves and/or garments.

In use, the NUV source can be made to any size and length. In air ducts, the embodiment shown in FIG. 2 item 6b would have the NUV source supported from the side, top or bottom of the duct so that its irradiation travels parallel to the airflow. For unique applications, a second embodiment FIG. 5 item 16 would have the NUV source and cylinder reflector supported inside the duct so that irradiation is perpendicular to the airflow. An example of this embodiment would be a NUV source positioned in the center of a tumbling dryer. All garments or objects or food stuffs would be irradiated during the drying or tumbling process for a length of time that would guarantee a high level of disinfection.

FIG. 2 illustrates the apparatus required for the disinfection and sterilization of airflow inside a large duct. NUV sources 7 precede an electrostatic precipitator (ESP) 9 by some distance 8 that permits a short action time to complete the destruction of the toxic gases or VSP's. A humidifier 10 may follow the precipitator with control sensors 11 so that the humidity of the exiting air can be selected and maintained. A fan(s) 12 may also be used to pressurize the exiting air so that a slight pressurization can be applied to a protected zone to prevent contaminated air from entering. Depending on the nature of the zone, restricting baffles (not shown) are used to assist in maintaining a positive pressure inside the protective zone.

FIG. 3a illustrates the NUV source 13 located inside the forward compartment of a vacuum cleaner or floor cleaning machine. The vacuum cleaner can be either a standup floor model or a canister model. It could also be any device that would support and carry the NUV source close to the floor. The significant part is that the NUV source with reflector 6 consists of the components as described in FIG. 1 b. FIG. 3b illustrates a preferred embodiment with the NUV source contained in a hand held wand. Sensing switches 14 can be included in this embodiment that shut off the NUV source when the wand is not directed correctly to the desired treatment surface.

FIG. 4a illustrates the NUV source(s) located above a conveyor that carries raw and unprepared food prior to kitchen preparation as well as industrial packaging assembly lines that carry products that require disinfection. The conveyor assembly 24 is designed to maximize the surface area exposed to the NUV source(s). In some cases, several sources 13 are required because the exposed surface of the food or product can not be changed to expose the entire surface during the illumination time of one NUV source. Tumblers or vibrators are typically used to change the orientation of the foodstuffs or parts as they move along the conveyor. However, a rotary tumbler similar to a cloth dryer with the NUV source located in the center would be the preferred embodiment for disinfecting leafy greens. FIG. 4b illustrates the NUV source(s) 13 located beside heat lamps 15 or other heating surfaces used to keep the food hot on a serving counter prior to being delivered from the kitchen to the customer. In another embodiment, the NUV source is used to irradiate cool or cold foods, so heat lamps 15 are not used.

FIG. 5 illustrates the NUV source located inside an air sterilization apparatus that provides air for remote and separate operation tables. The NUV source 16 is located inside a UV reflector chamber 17 in order to reduce the loss of UV photons. A light trap 18 stops the UV light prior to the turning vanes 19 that direct the air flow vertically downward onto the operation site. A diffuser 20 ensures that the airflow is uniform across the duct. A high E field electrostatic precipitator (ESP) 21 follows the diffuser to remove particulates and reduce any ozone to oxygen. The airflow then passes through a second diffuser and humidifier 22 to ensure that the airflow is uniform across the duct and that the humidity level is controlled to some preset value.

FIG. 6 illustrates how the air sterilization apparatus would be used in conjunction with a remote operation site, where the doctor is using remote controlled surgical instruments that are inside the sterilized air zone.

FIG. 7 illustrates the airflow pattern using CFD computational fluidic design to ensure that the air above the operation zone is uniform and prohibits contaminated air from entering the protected zone.

FIGS. 8 through 15 are discussed in the technical and background sections of this specification.

Although the preferred embodiments of the present invention have been described herein, the above description is merely illustrative. Further modification of the invention herein disclosed will occur to those skilled in the respective arts. All such modifications are deemed to be within the scope of the invention as defined by the appended claims and not limited thereto.

What is claimed is:

1. A process for destroying a DNA or RNA of a microorganism on a substance or surface comprising the steps of:
   generating photons of at least one wavelength corresponding to a peak absorption wavelength of DNA or RNA, the at least one wavelength being at least one of 222 nm and 282 nm;
   directing the photons to the substance or surface to be disinfected, whereby the photons are selected to destroy a plurality of chemical bonds within the DNA or RNA of the microorganisms; and
   wherein the substance or surface to be disinfected is human or animal skin.

2. The process of claim 1 further comprising the step of providing an new ultra violet source for generating the photons.

3. The process of claim 1 wherein the directing step is performed by reflecting the photons to a desired surface.

4. The process of claim 1 wherein the step of directing the photons further comprises the step of providing 540 kJ/mole of photon energy to the substance or surface to be disinfected.

5. The process of claim 1 wherein the step of directing the photons further comprises directing the photons to provide a radiant dose energy of 40 mJ/cm$^2$ to the substance or surface to be disinfected.

6. The process of claim 1 wherein the step of directing the photons further comprises directing the photons to provide a radiant dose energy of 60 mJ/cm$^2$ to the substance or surface to be disinfected.

7. The process of claim 1 wherein the step of directing the photons further comprises providing a radiant dose energy of 10 mJ/cm$^2$ to the substance or surface to be disinfected.

8. The process of claim 1 further comprising the step of selecting a source for generating the photons, the source for generating the photons selected to produce an irradiance of approximately 100 mw/cm$^2$ or less.

9. The process of claim 1 wherein the step of directing the photons further comprises exposing the substance or surface to be disinfected to the generated photons for less than 0.1 second.

10. The process of claim 1 further comprising the step of selecting a source for generating the photons, wherein the source for generating photons is a hand held lamp, and wherein the step of directing the photons further comprises the step of waving the hand held lamp over the surface or substance to be disinfected, exposing the surface or substance to the generated photons for approximately 0.1 second or less.

11. The process of claim 1 wherein the at least one wavelength is 222 nm and wherein the step of generating photons further comprises generating photons at a wavelength of 207 nm.

12. A process for destroying a DNA or RNA of a microorganism on a substance or surface comprising the steps of:
generating photons of at least two single line wavelengths corresponding to a peak absorption wavelength of DNA or RNA, the at least two single line wavelengths being at least two of 222 nm, 254 nm and 282 nm; and
directing the photons to the substance or surface to be disinfected, whereby the photons are selected to destroy a plurality of chemical bonds within the DNA or RNA of the microorganisms.

13. The process of claim 12 wherein the directing step is performed by reflecting the photons to a desired surface.

14. The process of claim 12 wherein the step of directing the photons further comprises the step of providing 540 kJ/mole of photon energy to the substance or surface to be disinfected.

15. The process of claim 12 wherein the step of directing the photons further comprises directing the photons to provide a radiant dose energy of 40 mJ/cm$^2$ to the substance or surface to be disinfected.

16. The process of claim 12 wherein the step of directing the photons further comprises directing the photons to provide a radiant dose energy of 60 mJ/cm$^2$ to the substance or surface to be disinfected.

17. The process of claim 12 wherein the step of directing the photons further comprises providing a radiant dose energy of 10 mJ/cm$^2$ to the substance or surface to be disinfected.

18. The process of claim 12 further comprising the step of selecting a source for generating the photons, the source for generating the photons selected to produce an irradiance of approximately 100 mw/cm$^2$ or less.

* * * * *